US012496021B1

(12) United States Patent
Hruschka et al.

(10) Patent No.: US 12,496,021 B1
(45) Date of Patent: Dec. 16, 2025

(54) OPTIMIZED ADJUSTMENT OF A PATIENT COUCH IN THE VERTICAL DIRECTION

(71) Applicant: Siemens Healthineers AG, Forchheim (DE)

(72) Inventors: Klaus Hruschka, Erbendorf (DE); Harald Graf, Speichersdorf (DE); Lutz Weiss, Bayreuth (DE); Roland Schoecklmann, Kastl (DE); Paul Weidner, Pressath (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 0 days.

(21) Appl. No.: 19/234,361

(22) Filed: Jun. 11, 2025

(30) Foreign Application Priority Data

Jun. 13, 2024 (DE) ..................... 10 2024 205 454.2

(51) Int. Cl.

| | |
|---|---|
| ***A61B 6/00*** | (2024.01) |
| ***A61B 5/00*** | (2006.01) |
| ***A61B 5/055*** | (2006.01) |
| ***A61B 6/04*** | (2006.01) |

(52) U.S. Cl.
CPC ............ *A61B 6/0487* (2020.08); *A61B 5/055* (2013.01); *A61B 5/704* (2013.01); *A61B 6/548* (2013.01)

(58) Field of Classification Search
CPC ......... A61B 6/00; A61B 6/0487; A61B 5/055; A61B 5/704; A61B 6/548
See application file for complete search history.

(56) References Cited

U.S. PATENT DOCUMENTS

| | | | | |
|---|---|---|---|---|
| 4,671,728 A * | 6/1987 | Clark .................. | A61B 6/0487 414/284 |
| 2006/0167356 A1* | 7/2006 | Everett ................ | A61B 6/0487 600/407 |
| 2015/0308467 A1 | 10/2015 | Brokes et al. | |
| 2018/0329422 A1* | 11/2018 | Biber .................. | G05D 1/0088 |

FOREIGN PATENT DOCUMENTS

| | | |
|---|---|---|
| DE | 102012222637 A1 | 6/2014 |
| DE | 102021210095 A1 | 3/2023 |

OTHER PUBLICATIONS

German Office Action and English translation thereof for German Application No. 10 2024 205 454.2 mailed Jan. 17, 2025.

* cited by examiner

*Primary Examiner* — Fredrick C Conley
(74) *Attorney, Agent, or Firm* — Harness, Dickey & Pierce, P.L.C.

(57) ABSTRACT

A medical facility has a patient couch having a position that can be adjusted in the vertical direction via a drive. An operating method for a medical facility with a patient couch having a position that can be adjusted in the vertical direction via a drive includes actuating the drive in response to receiving, by a control facility, a travel command from an operator to move the patient couch upward, the actuating including, moving the patient couch downward during an initial period, and actuating the drive in a lifting period immediately following the initial period such that the drive moves the patient couch upward.

15 Claims, 4 Drawing Sheets

OPTIMIZED ADJUSTMENT OF A PATIENT COUCH IN THE VERTICAL DIRECTION

CROSS-REFERENCE TO RELATED APPLICATION(S)

The present application claims priority under 35 U.S.C. § 119 to Germany Patent Application No. 10 2024 205 454.2, filed Jun. 13, 2024, the entire contents of which is incorporated herein by reference.

Independent of the grammatical term usage, individuals with male, female or other gender identities are included within the term.

SUMMARY

One or more example embodiments is based on an operating method for a medical facility with a patient couch having a position that can be adjusted in the vertical direction via a drive, wherein, whenever a control facility receives a travel command from an operator on the basis of which the patient couch is to be moved upward, it actuates the drive in response to the travel command in such a way that the drive moves the patient couch upward.

One or more example embodiments is further based on a control program for a control facility of a medical facility with a patient couch having a position that can be adjusted in the vertical direction via a drive, wherein the control program comprises machine code which can be processed directly by the control facility, wherein processing the machine code by the control facility causes the control facility to execute such an operating method.

One or more example embodiments is further based on a control facility of a medical facility with a patient couch having a position that can be adjusted in the vertical direction via a drive, wherein the control facility is programmed with such a control program so that the control facility executes such an operating method.

One or more example embodiments is further based on a medical facility with a patient couch having a position that can be adjusted in the vertical direction via a drive, wherein the medical facility has such a control facility, which, to adjust the patient couch in the vertical direction, executes such an operating method.

BRIEF DESCRIPTION OF THE DRAWINGS

Features and advantages of example embodiments and the manner in which they are achieved will become clearer and more plainly comprehensible in conjunction with the following description in conjunction with the drawings. The drawings show in schematic representation.

DETAILED DESCRIPTION

Figure 1:
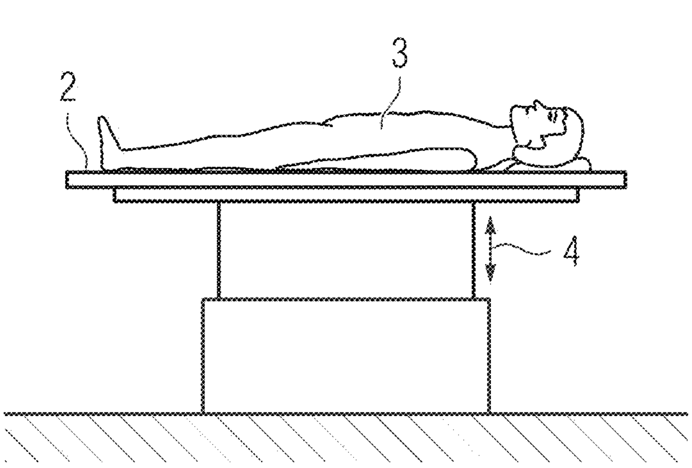
FIG. 1 illustrates a medical facility according to one or more example embodiments.

Various imaging medical modalities, for example CT systems, C-arm systems and MR systems, have a standard mounting location for vertically adjustable patient couches.

In some cases, a drive that acts on the patient couch via a self-locking gear is used for the lifting axis of a patient couch. The use of such a gear has various advantages, but also has various disadvantages.

An advantage is that an independent brake is not required to secure the patient couch at a specific height. Instead, it is only necessary to disconnect the power supply to the drive. A further advantage is that an electronically actuated brake cannot interfere with the magnetic field of a magnetic resonance system. A further advantage is the relatively low cost. Furthermore, only a few parts are susceptible to failure and few service calls are required.

One disadvantage is that the efficiency is relatively low. For example, it can be in the range between 20% and 25%. This means a relatively high drive power is required. This also applies to the entire remaining power supply, such as a power supply unit, the dimensions of an inverter feeding the drive and, in the case of a mobile medical facility (also referred to as a mobile medical device), an inbuilt battery.

The situation is most problematic when various circumstances coincide that require particularly high torque and/or particularly high power. Such a circumstance occurs when it is necessary to increase a particularly high load. Such a case can in particular occur when a patient is lying on the patient couch and the patient has a large body mass. A further circumstance occurs when the patient couch has not been moved for a certain period before being moved upward. This is because, in this case, the lubricating oil, which lubricates the contact surfaces of the drive train—for example toothing—and thus significantly reduces frictional force, is pressed out of the contact surfaces of the drive train. In this case, there is therefore direct metal-to-metal contact at the contact surfaces. An oil film only builds up again during travel. A further circumstance occurs if the lubricating oil is at a relatively lower temperature, as the lubricating oil is then more viscous and thicker, so that it takes longer for the oil film to build up. If these circumstances occur at the same time, the drive may not start.

To solve these problems, it is of course possible to dimension the energy supply accordingly. In this case, however, the energy supply has to be very large and this is associated with a corresponding volume and corresponding costs.

One or more example embodiments creates possibilities via which a reliable start-up of the drive can be achieved even when the above-described disadvantageous circumstances occur at the same time.

The object is achieved by an operating method with the features of claim 1. Advantageous embodiments of the operating method are the subject matter of the dependent claims 2 to 7.

According to one or more example embodiments, an operating method of the type mentioned in the introduction is embodied in that, whenever the control facility (also referred to as a controller) receives a travel command from an operator on the basis of which the patient couch is to be moved upward, it does not immediately actuate the drive in such a way that the drive moves the patient couch upward, but, in response to the travel command, initially actuates the drive in such a way that the drive moves the patient couch downward during an initial period and only then does it actuate the drive in a lifting period immediately following the initial period in such a way that the drive moves the patient couch upward.

Moving the patient couch downward at the start of the movement process means the weight of the patient couch and the patient lying on the patient couch does not have to be overcome to move the patient couch. All other circumstances being equal, this therefore requires a lower drive power than would be necessary to move the patient couch upward. However, the oil film builds up during the downward movement of the patient couch. As a result, in addition to the friction force, the weight of the patient couch and the patient lying on the patient couch has to be overcome when the patient couch is subsequently moved upward. However, with regard to the friction force, it is no longer necessary to overcome the high frictional force that occurs with metal-to-metal sliding. Instead, it is only necessary to overcome the considerably lower frictional force when the oil film that significantly reduces friction is present between the metal surfaces.

As a result, it is possible to dimension the energy supply of the drive as relatively small while still ensuring reliable start-up of the drive even during a lifting movement (i.e. when the patient couch is lifted upward) with a high load.

The extent by which the patient couch is moved downward during the initial period can be determined as required. In many cases, this extent can be easily set so small that it is not noticed by a patient lying on the patient couch or by the operator.

As already mentioned, a further disadvantageous circumstance is that, at least at the start of a travel movement, the lubricating oil can be relatively cold, and thus relatively viscous. Although the procedure according to one or more example embodiments ensures that the drive starts up, i.e. the lifting movement begins, it can happen that the lubricating effect of the lubricating oil is not yet optimal and therefore the drive is overloaded when the patient couch is moved upward, i.e. during the lifting period. To avoid this, during the lifting period, the control facility iteratively repeatedly actuates the drive in such a way that a lifting speed at which the patient couch is moved upward is increased continuously or in stages. However, in this case, the control facility performs two checks. Firstly, the control facility checks whether the lifting speed reaches a predetermined setpoint speed. Secondly, the control facility checks whether an electrical operating variable of the drive reaches a predetermined limit value. The control facility stops increasing the lifting speed as soon as the lifting speed reaches the predetermined setpoint speed or the electrical operating variable of the drive reaches the predetermined limit value. The electrical operating variable of the drive can be the current, the voltage, the power (i.e. the product of current and voltage, possibly taking into account a phase offset) or an operating frequency of the supplying inverter, as required.

Although the lifting speed is increased to the setpoint speed if possible, the increase in the lifting speed is stopped before the setpoint speed is reached as soon as the electrical operating variable of the drive reaches the predetermined limit value. Therefore, this procedure can reliably prevent overloading of the drive.

Of course, if the control facility receives a corresponding travel command from the operator, it must also be possible to move the patient couch downward by a corresponding actuation of the drive. Accordingly, whenever it receives a travel command from an operator on the basis of which the patient couch is to be moved downward, it controls the drive in response to the travel command during a lowering period in such a way that the drive moves the patient couch downward.

In order to be able to initially move the patient couch downward on receipt of a travel command on the basis of which the patient couch is to be moved upward, the corresponding downward travel path must be available at the time of receipt of this travel command. There are various options for reliably providing this travel path.

One option is that, when the patient couch is moved downward, the control facility stops the actuation of the drive as soon as the patient couch reaches a predetermined minimum distance to a lowest possible position.

A further option is that, when the patient couch is moved downward, the control facility actuates the drive at least in a final period immediately following the lowering period in such a way that the drive moves the patient couch upward if, during the lowering period, the patient couch is moved downward to a position which is less than a minimum distance to a lowest possible position.

In many cases, the drive drives a helical worm shaft in order to adjust the patient couch in the vertical direction. In this case, the control facility is preferably embodied in such a way that it terminates the final period as soon as the drive has rotated the worm shaft by a predetermined first angle of rotation, in particular by a maximum of 360°. This ensures that, after the final period, a predetermined second angle of rotation is always available for starting the drive when the patient couch is moved downward during the initial period.

Preferably, the control facility is further embodied in such a way that it terminates the initial period as soon as the drive has rotated the worm shaft by the predetermined second angle of rotation and that the second angle of rotation is at most as large as the first angle of rotation. This ensures that the initial downward movement of the patient couch is reversed into an upward movement in good time before the patient couch reaches its lowest possible position.

Regardless of the specific procedure when moving the patient couch downward, the control facility is preferably embodied in such a way that it terminates the initial period as soon as the drive has rotated the worm shaft by a predetermined angle of rotation, in particular by a maximum of 360°.

The angle of rotation of 360° is in particular important because the worm shaft is often oriented horizontally and runs in an oil bath. Thus, on the performance of a (1) complete revolution it can never reliably be ensured that the entire circumference of the worm shaft is coated with lubricating oil.

The object is further achieved by a control program with the features of claim 8. According to one or more example embodiments, the processing of the control program causes the control facility to execute an operating method according to one or more example embodiments.

The object is further achieved by a control facility with the features of claim 9. According to one or more example embodiments, the control facility is programmed with a control program according to one or more example embodiments so that the control facility executes an operating method according to one or more example embodiments.

The object is further achieved by a medical facility (also referred to as a medical device) with the features of claim 10. According to one or more example embodiments, the control facility is embodied as a control facility according to one or more example embodiments.

The medical facility preferably has a self-locking gear, which is driven by the drive to adjust the patient couch in the vertical direction. The self-locking gear can in particular have a helical worm shaft.

According to FIG. 1, a medical facility 1 has a patient couch 2. A patient 3 can be supported on the patient couch 2. As indicated in FIG. 1 by a double arrow 4, the position of the patient couch 2 can be adjusted in the vertical direction. Therefore, the patient couch 2 can be moved upward and downward in the vertical direction. According to FIG. 2, the patient couch 2 is moved, i.e. its position is adjusted in the vertical direction, via a drive 5. As a rule, the drive 5 acts on the patient couch 2 via a gear 6, which is driven by the drive 5 to adjust the patient couch 2 in the vertical direction. The gear 6 can in particular be a self-locking gear, for example a worm gear as shown in FIG. 3, which has a helical worm shaft 7 and a gear wheel 8. In this case, the drive 6 rotates the worm shaft 7, which in turn acts on the gear wheel 8. The gear wheel 8 acts directly or indirectly on the patient couch 2.

Figure 2:
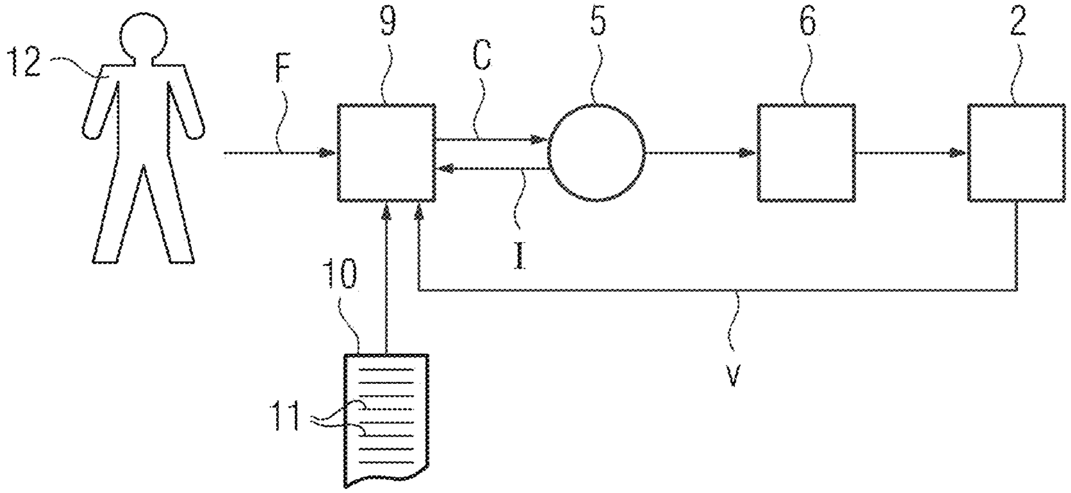
FIG. 2 illustrates a control facility and a drive train according to one or more example embodiments.
Figure 3:
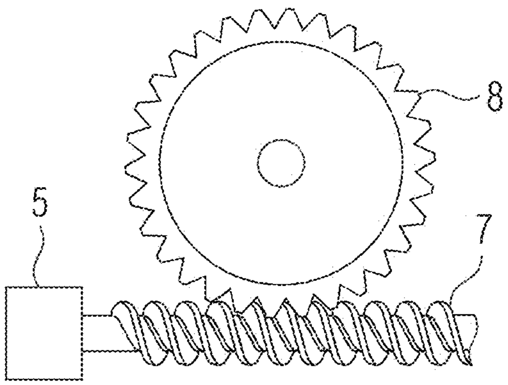
FIG. 3 illustrates a part of a drive train according to one or more example embodiments.

To actuate (inter alia) the drive 5, the medical facility 1 according to FIG. 2 has a control facility 9. The control facility 9 is programmed with a control program 10. The control program 10 comprises machine code 11, which can be processed by the control facility 9. The programming of the control facility 9 with the control program 10 or—synonymously—the processing of the machine code 11 by the control facility 9 causes the control facility 9 to adjust the patient couch 2 in the vertical direction by executing an operating method which is explained in more detail below in conjunction with FIG. 4.

Figure 4:
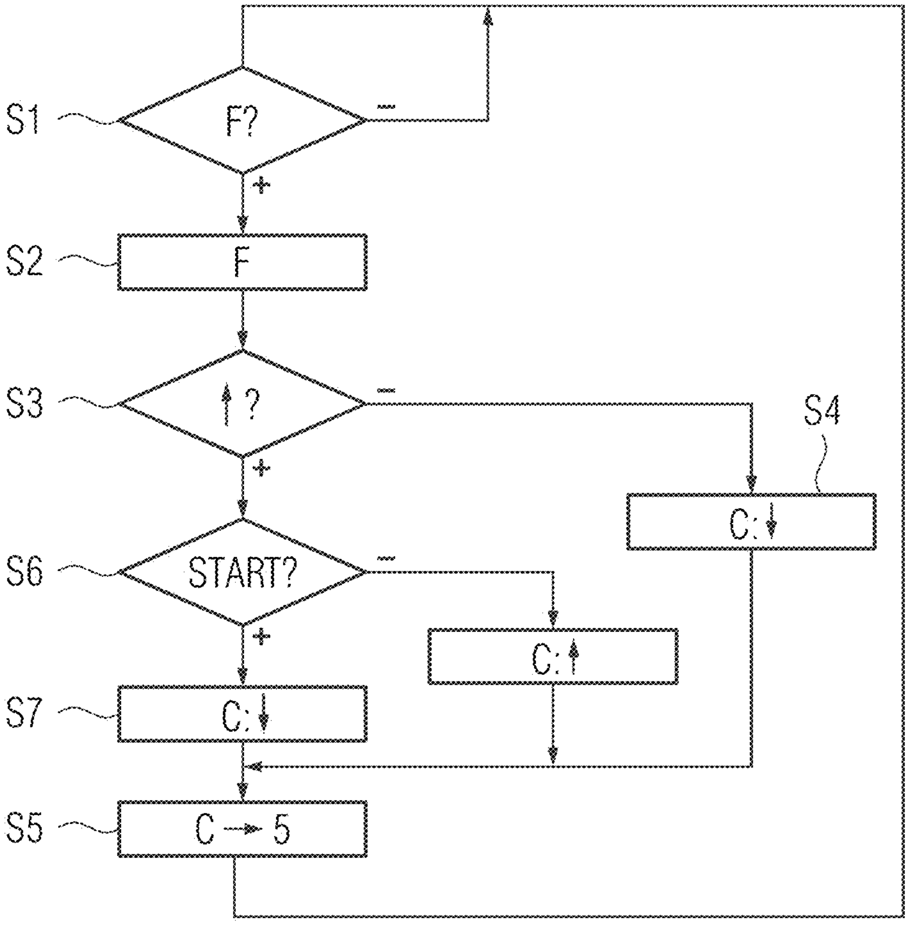
FIG. 4 illustrates a flowchart according to one or more example embodiments.

According to FIG. 4, the control facility 9 checks in a step S1 whether an operator 12 has given it a travel command F to move the patient couch 2 vertically. The control facility 9 repeats step S1 until it is given a travel command F. If a travel command F is given here, the control facility 9 accepts the travel command F in a step S2.

In a step S3, the control facility 9 checks whether the travel command F is a travel command to move the patient couch 2 upward. If this is not the case, the control facility 9 proceeds to step S4. In step S4, the control facility 9 ascertains an actuation C for the drive 5 on the basis of which the drive 5 moves the patient couch 2 downward. In a step S5, the control facility 9 controls the drive 5 in accordance with the ascertained actuation C. From step S5, the control facility 9 returns to step S1.

On the other hand, if the travel command F is a travel command to move the patient couch 2 upward, the control facility 9 checks in a step S6 whether the travel command F has just been given, i.e. if it entails the start of a travel movement of the patient couch 2. If this is the case, the control facility 9 proceeds to a step S7. In step S7, the control facility 9 ascertains an actuation C for the drive 5 on the basis of which the drive 5 moves the patient couch 2 downward, i.e. in the opposite direction to the actually desired direction of travel. The control facility 9 then proceeds to step S5. On the other hand, if this does not entail the start of an upward travel movement of the patient couch 2, the control facility 9 proceeds from step S6 to step S8. In step S8, the control facility 9 ascertains an actuation C for the drive 5 on the basis of which the drive 5 moves the patient couch 2 upward, i.e. in the actually desired direction of travel. The control facility 9 then returns to step S5.

Thus, the procedure in FIG. 2 has the effect that whenever the control facility 9 receives a travel command F from the operator 12 on the basis of which the patient couch 2 is to be moved upward, it initially actuates the drive 5 in response to the travel command F in such a way that the drive 5 moves the patient couch 2 downward and only then does it actuate the drive 5 in such a way that the drive 5 moves the patient couch 5 upward.

Figure 5:
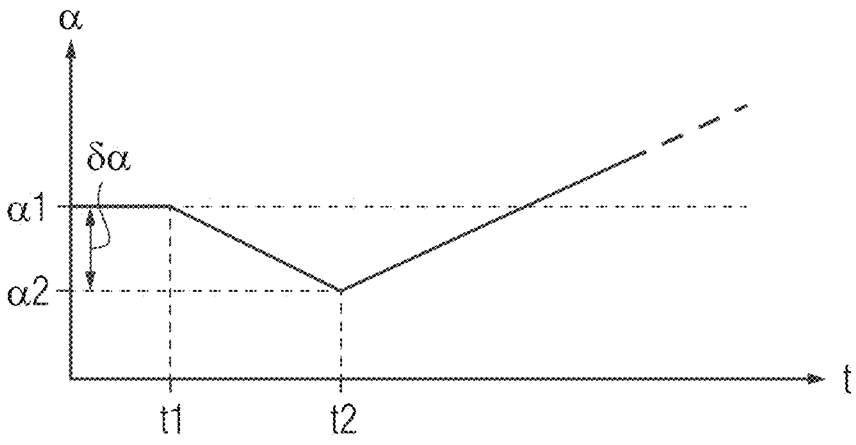
FIG. 5 illustrates a timing diagram according to one or more example embodiments.

This procedure is shown again in FIG. 5 in the form of a timing diagram in which the angular position $\alpha$ of the worm shaft 7 is shown by way of example as a function of time t. The greater the angular position $\alpha$ of the worm shaft 7, the further the patient couch 2 is moved upward in the present case.

The travel command F to move the patient couch 2 upward is given to the control facility 9 at a time t1. At time t1, the worm shaft 7 has an initial angular position $\alpha$1. Starting at with time t1, the worm shaft 7 is rotated to an angular position $\alpha$2 that is less than the initial angular position $\alpha$1. The angular position $\alpha$2 is reached at a time t2. Once the angular position $\alpha$2 is reached at time t2, the worm shaft 7 is rotated to angular positions a that increase, not only beyond the angular position $\alpha$2, but also beyond the angular position $\alpha$1. Therefore, the patient couch 2 is moved upward. The period from time t1 to time t2 is referred to below as the initial period. The period starting at time t2 is referred to below as the lifting period. The lifting period lasts as long as the patient couch 2 is moved upward. It is evident that the lifting period immediately follows the initial period.

The extent $\delta\alpha$ by which the angular position $\alpha$2 is less than the angular position $\alpha$1 can be determined as required. As a rule, the extent $\delta\alpha$ is less than 360°, often even considerably less than 360, for example 180° or less, 120° or less, or 90° or less. In some cases, it can be possible that the initial period as such is determined and the extent $\delta\alpha$ as such is accordingly not fixed. In other cases, it is possible that the extent $\delta\alpha$ as such is predetermined so that reaching angular position $\alpha$2 as such, i.e. the rotation of the worm shaft 7 by a predetermined angle of rotation as such terminates the initial period.

Figure 6:
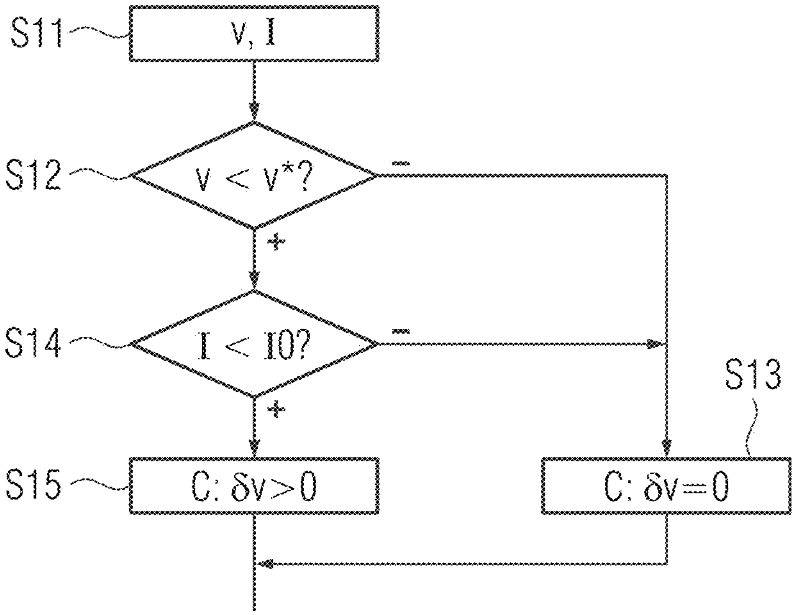
FIG. 6 illustrates a flowchart according to one or more example embodiments.

The following describes a currently preferred implementation of step S8 in conjunction with FIG. 6.

According to FIG. 6, a lifting speed v and an electrical operating variable I of the drive 5 become known to the control facility 9 in a step S11. The lifting speed v is the speed at which the patient couch 2 is moved upward. In the present case, the electrical operating variable I is supplied to the drive 5. However, different operating variables are also possible. As a rule, the operating variable I is given to the control facility 9 as a measured variable or derived by the control facility 9 from measured variables. The lifting speed v can be measured or ascertained by the control facility 9, for example from a sequence of captured height positions of the patient couch 2 or from actual position values of the drive 5.

In a step S12, the control facility 9 checks whether the lifting speed v is less than a predetermined setpoint speed v*. The setpoint speed v* can in principle be made known to the control facility 9 in any manner. For example, it can be defined in the control program 10 or defined during commissioning of the medical facility 1 or given anew to the control facility 9 by the operator 12 at any time during operation.

If the lifting speed v is not less than the setpoint speed v*, the lifting speed v has reached the setpoint speed v*. In this case, the control facility 9 proceeds to a step S13. In step S13, the control facility 9 ascertains the actuation C for the drive 5 in such a way that a change in speed $\delta$v has the value 0, i.e. the lifting speed v is maintained. Otherwise, the control facility 9 proceeds to a step S14.

In step S14, the control facility 9 checks whether the electrical operating variable I is less than a predetermined limit value 10. The limit value 10 can in principle be made known to the control facility 9 in any manner. The above statements relating to the setpoint speed v* apply analogously.

If the electrical operating variable I is less than the limit value 10, the control facility 9 proceeds to a step S15. In step S15, the control facility 9 ascertains the actuation C for the drive 5 in such a way that the change in speed δv has a value above 0, i.e. the lifting speed v is increased. The increase can take place continuously or in stages. Otherwise, the control facility 9 proceeds to step S13.

As can be seen in FIG. 4, whenever the control facility 9 receives a travel command F from the operator 12 on the basis of which the patient couch 2 is to be moved downward, it actuates the drive 5 in response to the travel command F in step S4 in such a way that the drive 5 moves the patient couch 2 downward. However, step S4 or the integration of step S4 into the flowchart in FIG. 4 advantageously takes place in a specific manner.

Figure 7:
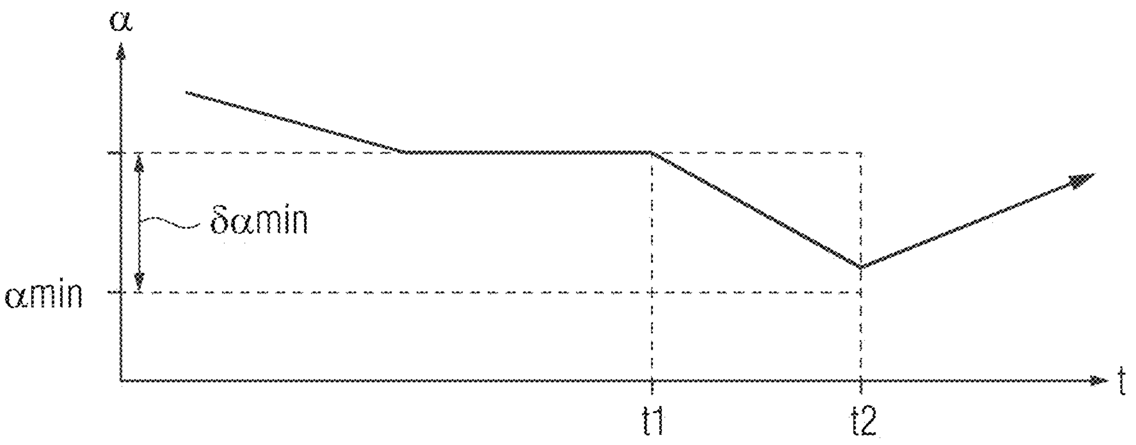
FIGS. 7 and 8 illustrate timing diagrams.

For example, it is possible that, although the control facility 9 initially ascertains the actuation C of the drive 5 in such a way that the drive 5 moves the patient couch 2 downward, the control facility 9 checks according to the embodiment in FIG. 7 whether the patient couch 2 reaches a predetermined minimum distance to a lowest possible position. If the patient couch 2 reaches the minimum distance to the lowest possible position, the control facility 9 stops the actuation of the drive 5 and thus the downward movement of the patient couch 2. This also applies if the control facility 9 continues to be given the travel command F to move the patient couch 2 downward.

The lowest possible position is the position from which further downward movement of the patient couch 2 is no longer possible, for example because a mechanical stop is reached. The minimum distance is determined in such a way that it is at least as large as the downward travel path of the patient couch in step S7. The minimum distance is preferably slightly larger than this travel path. The corresponding situation is shown in FIG. 7 for the angular position α of the worm shaft 7. αmin is the angular position of the worm shaft 7 at which the patient couch 2 reaches the lowest possible position. δαmin is an angle of rotation of the worm shaft 7 that corresponds to the minimum distance. However, the situation shown in FIG. 7 is also applicable for cases in which the drive 5 acts on the patient couch 2 in a different way.

Figure 8:
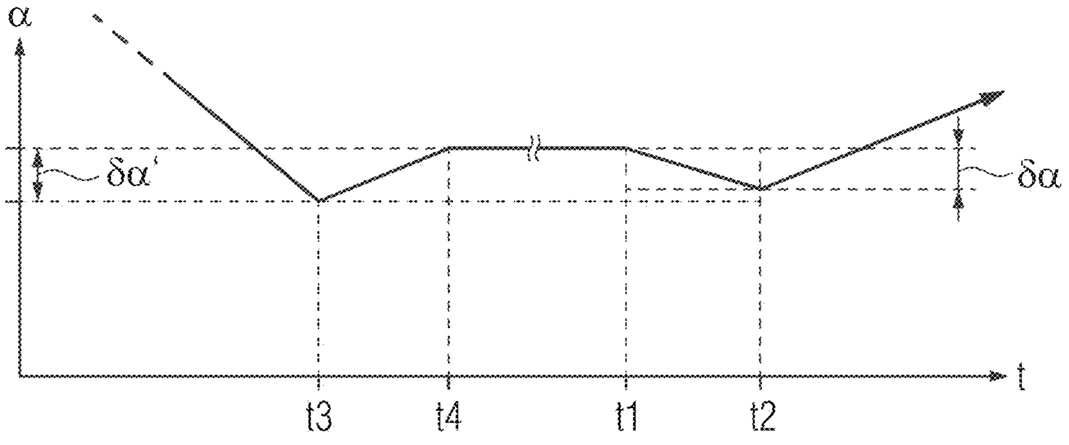

A further option is explained below in conjunction with FIG. 8. The angular position α of the worm shaft 7 is also shown in FIG. 8. The situation shown in FIG. 8 is also valid for cases in which the drive 5 acts on the patient couch 2 in a different way.

According to FIG. 8, the control facility 9 initially controls the drive 5 in response to a travel command F to move the patient couch 2 downward in such a way that the drive 5 moves the patient couch 2 downward. The travel command F to move the patient couch 2 downward is given at a time t3. At this time, the actual downward movement of the patient couch 2 is stopped. Time t3 represents the end of a period which is referred to below as the lowering period. However, when the travel command F is stopped i.e. when the lowering period is stopped, the control facility 9 controls the drive 5 for a short period in such a way that the drive 5 moves the patient couch 2 upward. This period, which lasts until a time t4, is referred to below as the final period. The final period immediately follows the lowering period. The corresponding procedure, i.e. the upward movement of the patient couch 2 during the final period, can, for example, be implemented in the NO branch of step S1 in FIG. 4, i.e. if, in the sequence of steps S1-S2-S3-S4-S5, the travel command F is no longer given when step S1 is executed again and therefore there is a transition to the NO branch of step S1.

It is possible that the control facility 9 always executes the procedure explained above in conjunction with FIG. 8. However, it is also possible that the control facility 9 only executes this procedure if the patient couch 2 is moved downward during the lowering period to a position that is less than the minimum distance to the lowest possible position.

During the final period, the patient couch 2 is moved upward. In the case of the worm shaft 7, this corresponds to an extent δα'.

Analogous to the extent δα by which the angular position α2 in FIG. 5 is less than the angular position α1, the corresponding extent δα' by which the drive 5 moves the patient couch 2 upward during the final period can also be determined as required within the context of the embodiment in FIG. 8. As a rule, the extent δα' is less than 360°, often even considerably less than 360, for example 180° or less, 120° or less, or 90° or less. In some cases, it can be possible that the final period as such is determined and the extent δα' as such is accordingly not fixed. In other cases, it is possible that the extent δα' is predetermined, so that reaching the corresponding angular position as such, i.e. the rotation of worm shaft 7 by a predetermined angle of rotation as such, terminates the initial period. In the latter case, the angle of rotation corresponding to the extent δα' must be at least as large as the angle of rotation corresponding to the extent. Preferably, the angle of rotation corresponding to the extent δα' is (slightly) larger than the angle of rotation corresponding to the extent δα.

Example embodiments have many advantages. In particular, the drive 5 and the energy supply of the drive 5 can be designed as smaller than in the prior art.

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a Graphics Processing Unit (GPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

Although the invention has been illustrated and described in detail by the preferred exemplary embodiments, it is not restricted by the disclosed examples and a person skilled in the art can derive other variations herefrom without departing from the scope of the invention.

The invention claimed is:

1. An operating method for a medical facility with a patient couch having a position that can be adjusted in a vertical direction via a drive, the method comprising:
- actuating the drive in response to receiving, by a control facility, a travel command from an operator to move the patient couch upward, the actuating including,
  - moving the patient couch downward during an initial period, and
  - actuating the drive in a lifting period immediately following the initial period such that the drive moves the patient couch upward.

2. The operating method of claim 1, wherein the moving the patient couch downward includes,
- actuating the drive in response to the travel command during a lowering period such that the drive moves the patient couch downward and actuating the drive at least in a final period following the lowering period such that the drive moves the patient couch upward if, during the lowering period, the patient couch is moved downward to a position which is less than a minimum distance from a minimum position.

3. The operating method of claim 2, wherein to adjust the patient couch in the vertical direction, the drive drives a helical worm shaft and the control facility terminates the final period when the drive has rotated the worm shaft by a predetermined first angle of rotation.

4. The operating method of claim 3, wherein the control facility terminates the initial period when the drive has rotated the worm shaft by a predetermined second angle of rotation and the second angle of rotation is less than or equal to the first angle of rotation.

5. The operating method of claim 2, wherein to adjust the patient couch in the vertical direction, the drive drives a helical worm shaft and the control facility terminates the initial period when the drive has rotated the worm shaft by a predetermined angle of rotation.

6. The operating method of claim 1, wherein the moving the patient couch downward includes,
- actuating the drive in response to the travel command during a lowering period such that the drive moves the patient couch downward and stopping the actuation of the drive when the patient couch reaches a predetermined minimum distance from a minimum position.

7. A non-transitory computer readable medium for a control facility of a medical facility with a patient couch having a position that can be adjusted in the vertical direction via a drive, wherein the non-transitory computer readable medium comprises machine code, when executed by the control facility, causes the control facility to perform the method of claim 1.

8. A control facility of a medical facility with a patient couch having a position that can be adjusted in the vertical direction via a drive, the control facility comprising:
- the non-transitory computer readable medium of claim 7.

9. A medical facility comprising:
- a patient couch having a position that can be adjusted in the vertical direction via a drive; and
- the control facility of claim 8.

10. The medical facility of claim 9, further comprising:
- a self-locking gear configured to be driven by the drive to adjust the patient couch in the vertical direction.

11. The operating method of claim 1, the actuating the driving in a lifting period includes,
- iteratively actuating the drive such that a lifting speed at which the patient couch is moved upward is increased continuously or in stages,
- checking whether the lifting speed reaches a predetermined setpoint speed,
- checking whether an electrical operating variable of the drive reaches a predetermined limit value, and
- stopping a increase of the lifting speed when the lifting speed reaches the predetermined setpoint speed or the electrical operating variable of the drive reaches the predetermined limit value.

12. The operating method of claim 11, wherein the moving the patient couch downward includes,
- actuating the drive in response to the travel command during a lowering period such that the drive moves the patient couch downward and stopping the actuation of the drive when the patient couch reaches a predetermined minimum distance from a minimum position.

13. The operating method of claim 11, wherein the moving the patient couch downward includes,
- actuating the drive in response to the travel command during a lowering period such that the drive moves the patient couch downward and actuating the drive at least in a final period following the lowering period such that the drive moves the patient couch upward if, during the lowering period, the patient couch is moved downward to a position which is less than a minimum distance from a minimum position.

14. The operating method of claim 13, wherein to adjust the patient couch in the vertical direction, the drive drives a helical worm shaft and the control facility terminates the final period when the drive has rotated the worm shaft by a predetermined first angle of rotation.

15. The operating method of claim 14, wherein the control facility terminates the initial period when the drive has rotated the worm shaft by a predetermined second angle of rotation and the second angle of rotation is less than or equal to the first angle of rotation.

* * * * *